United States Patent [19]
Rånby et al.

[11] Patent Number: 5,175,087
[45] Date of Patent: Dec. 29, 1992

[54] METHOD OF PERFORMING TISSUE PLASMINOGEN ACTIVATOR ASSAY

[75] Inventors: Mats G. Rånby, Umeå ; Tor-Björn Wiman, Sollentuna, both of Sweden

[73] Assignee: Biopool International, Inc., Ventura, Calif.

[21] Appl. No.: 392,684

[22] Filed: Aug. 11, 1989

Related U.S. Application Data

[63] Continuation-in-part of Ser. No. 355,948, May 23, 1989, which is a continuation-in-part of Ser. No. 70,068, Jul. 6, 1987, abandoned.

[51] Int. Cl.⁵ .......................... A01N 1/02; C12Q 1/37; C12Q 1/56; G01N 33/72
[52] U.S. Cl. ...................................... 435/13; 435/2; 435/23; 436/66
[58] Field of Search ............... 435/2, 13, 23; 436/66

[56] References Cited

U.S. PATENT DOCUMENTS 4,534,972  8/1985  Lembach ............................... 424/86
4,780,419 10/1988  Uchida et al. ........................... 435/2

OTHER PUBLICATIONS

Ceresa, editor "Block and Graft Copolymerization", vol. 2 pp. 194–201 (1976).
Wiman et al., "Plasminogen Activator Release During Venous Stasis and Exercise as Determined by a New Specific Assay", Clin. Chem. Acta, vol. 127, pp. 279–288 (1983).
Chmielewska et al., "Evidence for a Rapid Inhibitor to Tissue Plasminogen Activator in Plasma", Thromb. Res., vol. 31, pp. 427–436 (1988).
Berne, et al., editor, Physiology, pp. 382–385 (1988).
Faulkner, W. R., edit. "Selected Methods for Small Clinical Chemistry Laboratory", Selected Methods of Clinical Chemistry, vol. 9, pp. 6–7 and 328).

*Primary Examiner*—David M. Naff
*Assistant Examiner*—Timothy J. Reardon
*Attorney, Agent, or Firm*—Jones, Askew & Lunsford

[57] ABSTRACT

The present invention relates to an improved method for collecting blood. The present invention also relates to a method of collecting blood whereby tissue plasminogen, tissue plasminogen activator inhibitor and other serine proteases, serine protease inhibitors and components that are produced or destroyed through the action of serine proteases in collected blood are stabilized. In addition, the present invention provides a method for collecting blood that reduces the hemolysis (lysis of red blood cells). Using the blood collecting method of the present invention, reliable control plasmas can be manufactured.

15 Claims, 2 Drawing Sheets

METHOD OF PERFORMING TISSUE PLASMINOGEN ACTIVATOR ASSAY

CROSS-REFERENCE TO RELATED APPLICATIONS

This application is a continuation-in-part of U.S. patent application Ser. No. 07/355,948 filed on May 23, 1989, which is a continuation-in-part of U.S. patent application Ser. No. 07/070,068 filed on Jul. 6, 1987, now abandoned.

TECHNICAL FIELD

The present invention relates to an improved method and device for collecting blood. More particularly, the present invention relates to a method of collecting blood whereby hemolysis is reduced and many blood components are stabilized. The present invention also relates to a sample collection device for collecting blood.

BACKGROUND

The term "control plasma" means a plasma with a predefined concentration of one or more blood components so that the plasma can be used as a control or standard for determining the presence or concentration of those components.

Blood collection

Blood is composed of blood cells suspended in a protein rich fluid called blood plasma. The blood cells are of three main types, erythrocytes (red blood cells), leucocytes (white blood cells) and thrombocytes (platelets). The blood plasma contains many proteins involved in hemostasis (functions that prevent bleeding while keeping the blood fluid), in immunological reactions and in a multitude of communication and transport functions.

Blood has the ability to clot, that is become non-fluid or coagulated. This function involves the thrombocytes and several blood plasma proteins, particularly fibrinogen and prothrombin. During the coagulation process, prothrombin is converted into thrombin, a highly specific protein degrading enzyme. Thrombin degrades fibrinogen to form fibrin monomers which spontaneously aggregate to form fibrin which is the main structural element of a blood clot. Efficient thrombin formation requires relative high levels of calcium ions. Furthermore, the activity of thrombin (and the activity of enzymes involved in generating thrombin) can be inhibited by protein inhibitors found in blood plasma.

Anticoagulated blood has been treated to prevent blood coagulation. This treatment involves adding substances like citrate or ethylenediaminotetraacetate (EDTA) that reduce the calcium ion concentration and/or adding substances like heparin that promote the activity of thrombin inhibitors.

One of the problems of blood collection is hemolysis. Hemolysis is characterized by a reddish coloration of the blood plasma due to rupture of red blood cells. The red blood cells, the erythrocytes, are composed of a cell membrane enclosing large amounts of a red, iron rich, oxygen carrying protein, hemoglobin. The membrane of red blood cells is basically of the same type as that of other cells, and it is envisaged that conditions that rupture the membranes of red blood cells also rupture the membranes of other blood cell, i.e. thrombocytes and leucocytes. Hemolysis is undesirable and should be avoided when collecting blood samples.

Blood plasma is obtained from anticoagulated blood after removal of the blood cells by centrifugation or by filtration as known by those commonly skilled in the art. After separation, one can determine if hemolysis has occurred by qualitative and/or quantitative determination of the red colored hemoglobin in the plasma.

Blood samples anticoagulated with citrate are typically collected using siliconized glass or plastic tubes containing one volume of 0.11 to 0.13 mol/L trisodium citrate into which nine volumes of blood is allowed to flow through a hypodermic needled which has been pushed through the skin and into a blood vessel, a vein or, less commonly, an artery, see Faulkner et al., Selected Methods for the Small Clinical Chemistry Laboratory, Selected Methods of Clinical Chemistry, *Amer. Assoc. for Clin. Chem.*, Washington, D.C., Vol. 9 (1982).

Tissue Plasminogen Activator and related proteins

Tissue plasminogen activator (tPA) a serine protease, is recognized as the key enzyme in plasmin mediated dissolution of fibrin in the circulatory tract. (For review see RÅanby, M. and Brandstrom, A., *Enzyme*, 40, 130–143 (1988)). Low blood levels of tPA activity in the blood predisposes for thrombosis, Nilsson, I. M. et al., *Br. Med. Journal*, 290, 1453–1456 (1985), and high levels of tPA predisposes for bleeding, Booth, N. A. et al., *Blood*, 61: 267–275 (1983)). Furthermore, tPA produced by cell culture techniques is now adminstered intravenously to patients suffering from circulatory obstructions, such as myocardial infarctions, to dissolve the fibrin component of the occlusion. Thus, there is need to accurately determine tPA levels in blood for diagnosis of thrombophilia and hemophilia and an anticipated need to monitor tPA activity levels during thrombolytic therapy.

Tissue plasminogen activator, in its active form, is continuously secreted from the endothelium into circulation from where it is rapidly removed, particularly by the liver. The circulatory half-life in humans is approximately 8 minutes. The level of tPA in the blood is determined by the release/uptake balance. Furthermore, the blood contains proteinase inhibitors, specifically plasminogen activator inhibitor type 1 (PAI-1) but also $\alpha_2$-antiplasmin ($\alpha_2$-AP) and C1-inhibitor that react with active tPA to form inactive tPA/inhibitor complexes. In the circulation, both active tPA and tPA/inhibitor complex are found. Typical basal level of active tPA is about 1 ng/mL (0.5 IU/mL) and inactive tPA about 5 ng/mL. (See Wiman, B. et al., *J. Lab. Clin. Med.*, 105, 265–270 (1985)).

When a blood sample is drawn, e.g. by venous puncture, and collected in a container, tPA continues to react with inhibitors whereby the tPA activity declines and soon becomes nonrepresentative of the tPA activity in the circulating blood. For technical reasons, tPA is usually not determined in whole blood but in the blood plasma where most of the tPA activity is found. To obtain blood plasma, an anticoagulant is added to the whole blood during collection. The anticoagulant solutions commonly used are sodium citrate, EDTA and heparin. However, these commonly used anticoagulants do not prevent reaction between tPA and inhibitors and therefore results of tPA activity assays are not free from sample collection artifacts. The instability of tPA activity in collected blood is a major obstacle for diagnostic and scientific advancement in the area of hemostasis.

At least three methods have been attempted to overcome the problem of tPA instability in collected blood. All three are found to have limitations.

1. Euglobulin precipitation. The isolated anticoagulated plasma is diluted 10 fold with water or weak (10 mmol/L) acetic acid to form a precipitate, which contains the tPA activity. The precipitate is collected as a centrifugation sedimented and the supernatant, which contains inhibitors, is discarded, Isacsson, S. and Nilsson, I. M., *Acta Chir Scand*, 138, 313-319 (1972). The disadvantages of the method are; i) tPA activity is lost during the time needed for plasma isolation and euglobulin precipitation; ii) the method is tedious; iii) recovery of tPA activity is incomplete and variable; and iv) the sample is left useless for most other purposes.

2. Blood acidification to approximately pH 4. To prevent reaction between tPA and inhibitors and to destroy antiplasmin activity, one volume 1 mol/L acetate buffer pH 3.9 is added to two volumes of anticoagulated blood and the plasma immediately isolated by centrifugation, Chmielewska et al., *Thromb. Res.*, 31, 427-436 (1983). The disadvantages of the method are: i) it takes some time before the blood is acidified during which tPA activity is lost; ii) the method is tedious; iii) it causes hemolysis; iv) it can cause dissociation of tPA-/inhibitor complexes; v) due to protein denaturation by low pH, the sample is left useless for most other purposes and; (vi) yields plasma samples in which precipitation and gelation occurs during freeze storage; and vii) the plasma sample is diluted about 1:2.

3. Using monoclonal antibody against the active site of tPA. The blood sample is collected in anticoagulant containing a monoclonal antibody directed against the active site of tPA which prevents reaction with inhibitors. After isolation of plasma, the amount of tPA-/monoclonal antibody complex is determined and taken as a measure of the amount of active tPA in the original sample. The disadvantages of the method are: i) does not measure tPA activity, but rather the amount of tPA with a free active site which may not be the same; ii) is expensive because of the antibodies; and iii) will, because of the antibodies, result in devices with limited stability.

The present invention provides a method and devise to collect blood in which the tPA activity can be accurately measured. The process has the following features: i) inhibits reaction between tPA and inhibitors without causing major dissociation of tPA/inhibitor complexes; ii) is convenient; iii) causes little or not hemolysis; iv) yields plasma samples that can be stored frozen; v) yields plasma samples that can be used for other testing; and v) is inexpensive.

SUMMARY OF THE INVENTION

In accordance with the present invention, an improved method of collecting blood is provided. The improved method stabilizes tPA activity in blood and allows determination of circulating levels of tPA activity. The method also stabilizes other serine proteases, serine protease inhibitors and components that are produced or destroyed through the action of serine proteases in collected blood. The method also stabilizes soluble fibrin and as well as other blood components such as fibrinogen, Factor V, Factor VIII, activated Factor VII and activated protein C. An important feature of the method is that, with few exceptions, it does not reduce the utility of the collected blood for analysis of other blood components.

The improved method of collecting blood comprises an immediate, minimally dilutive acidification of the blood from the physiological pH of about 7.3 to a pH between 5.0 and 6.5. This is accomplished by drawing blood into a container containing a small amount of relatively strong pH buffer. The buffer to blood ratio is preferably smaller than 1:4. An important feature of the invention is that it does not cause excessive dilution of the collected blood. Another important feature of the invention is that the lowering of the pH is immediate. In development of the method it was found that the reduction of pH to a suitable degree could be accomplished with strong pH buffer without causing excessive hemolysis. In fact, it was found that if the pH of the blood was lowered to about 6.0, then hemolysis was decreased. Furthermore, the hemolysis reduction was most pronounced at certain buffer strengths.

In a preferred mode of operation, the pH buffer is citrate buffer. Nine volumes of blood is collected in 1 volume of buffer. Other pH buffers, e.g. acetate, proprionate, borate, isocitrate, aconitate, oxalate, can be used without departing from the spirit of the invention. Di and tricarboxylic acids are preferred because of their calcium ion binding activity which provides anticoagulation in addition to that provided by acidification and relieves the need to include additional components for this function. Other modes of operations are envisaged as being within the scope of this invention. A smaller buffer to blood ratio can be used but requires higher buffer concentration to achieve the optimum effects. In addition, it is within the contemplation of the present invention that a solid buffer can be placed in the container so that when the blood is collected, the buffer will dissolve in the blood and thereby reduce the pH of the blood to the preferred range of 5.0 to 6.5.

In addition, it was found that certain surface active substances reduce hemolysis. These surface active substances are linear block copolymers with one hydrophobic, polyoxypropylene central section with two hydrophilic, polyoxyethylene side sections. To further reduce hemolysis of blood during the acidification of the blood, it has been found advantageous to add a surface active copolymer to the acidic buffer prior to blood collection. The surface active copolymer has the following general structure:

wherein a is an integer such that the hydrophobe represented by $(C_3H_6O)$ has a molecular weight of approximately 950 to 4000, preferably about 1750 to 3500, and b is an integer such that the hydrophile portion represented by $(C_2H_4O)$ constitutes approximately 50% to 95% by weight of the compound.

The present invention also includes a collection device comprising a tube with a relatively small amount of acidic buffer therein whereby when blood is introduced into the tube, the pH of the blood is immediately lowered to between 5.0 and 6.5. The preferable buffer is citrate.

Accordingly, it is an object of the present invention to provide an improved method of collecting blood.

It is another object of the present invention to provide an improved method of collecting blood without excess dilution and hemolysis wherein the pH of the blood is reduced to between 5.0 and 6.5.

Another object of the present invention is to provide a method of immediately lowering the pH of the blood.

It is another object of the present invention to provide a method of collecting blood in which the circulating levels of tPA activity and soluble fibrin can be determined.

Another object of the present invention is to provide a method of collecting blood that is suited for determination of a large number of blood components including but not restricted to components that are serine proteases, serine protease inhibitors and substances degraded by or generated through the action of serine proteases such as activated factor VII, activated protein C, antithrombin, fibrinogen, fibrinopeptide A and complement factor C3b.

Another object of the present invention is to provide a method for producing control plasma which has stabilized levels of tPA activity and soluble fibrin.

Another object of the present invention is to provide a method for producing control plasma by adding and/or analyzing for many blood components in blood plasma acidified to pH between 5.0 and 6.5.

Another object of the present invention is to provide a device with which the invention can be practiced.

Another object of the present invention is to provide a device with which blood can be collected where the degree of pH reduction of the collected blood is dependent on the amount of blood drawn into the tube.

It is an object of the present invention to provide an improved method of assaying plasminogen activator inhibitor activity.

It is another object of the present invention to provide a method of collecting blood or other biological fluid that will stabilize tPA activity.

Another object of the present invention is to provide a method of immediately lowering the pH of the blood with a minimum of hemolysis.

These and other objects, features and advantages of the present invention will become apparent after a review of the following detailed description of the disclosed embodiment and the appended claims.

DETAILED DESCRIPTION OF THE DISCLOSED EMBODIMENT

According to the present invention, blood is collected in a pH buffer which immediately lowers the pH of the collected blood from the physiological range 7.0 to 7.6 to a range of 5.0 to 6.5. This range was chosen because the present studies showed that pH below 6.5 was necessary to stabilize a model serine protease, tPA, and pH above 5.0 to prevent excessive hemolysis and denaturation of plasma proteins.

According to the present invention, the pH is reduced by collecting blood at a ratio of buffer volume to blood volume of less than approximately 1:4. A preferred ratio is 8 to 9.9 volumes blood in 2 to 0.1 volume buffer. An especially preferred ratio is approximately 1 part of buffer to 9 parts of blood. It is anticipated that other ratios of blood and buffer and other buffer substances can be used.

With the preferred ratio of 1 to 9 referred to above, the model buffer, citrate, should have a concentration which falls in the range 0.3 to 0.6 mol/L with a preferred range of 0.35 to 0.55 mol/L and a most preferred concentration of 0.45 mol/L and a pH that falls in the range 3.0 to 5.5 for the pH of the collected blood to fall in the range 5.5 to 6.5 after the blood has been added. The final concentrations of citrate buffer in the blood plasma after mixing should be between approximately 0.05 to 0.1 mol/L. A preferred final concentration of citrate buffer in the blood plasma after mixing is between approximately 0.065 to 0.085 mol/L with an especially preferred final concentration of between approximately 0.075 mol/L.

It is to be understood that the present invention includes the addition of whole blood to a solid buffer substance which, when mixed with the blood, would result in a lowering of the pH of the blood to the preferred pH range. Using the model buffer, citrate, this could be done by either mixing the appropriate amounts of citrate acid and trisodium citrate or by adding the citrate buffer at the appropriate pH and then lyophilizing the sample thereby reducing the liquid buffer to a readily soluble solid.

Without departing from the spirit of the invention, the ratio of buffer to blood can be altered as long as the buffer concentration is adjusted accordingly. For example, if 0.5 volumes, instead of 1 volume, of buffer is used together with 9 volumes of blood, then the buffer concentration should be twice as high.

Citrate buffer is used as a model buffer in describing the present invention. However, the invention is not restricted to citrate and other buffers can be used to practice the present invention. These include, but are not limited to, citrate buffer, acetate buffer, propionate buffer, borate buffer, isocitrate buffer, aconitate buffer, and oxalate buffer. When working with the model buffer substance, citrate, sodium ions have been used as counter ions, it is to be understood that other metal cations, including but not limited to, lithium and potassium can be used.

When the blood pH is immediately lowered from about 7.3 to the range of 5.0 to 6.5, many components of the blood are left unaltered which makes the present invention for collecting blood suited for analysis of those components. The present invention is particularly suited for obtaining blood samples for determination of serine proteases, serine protease inhibitor and components that are produced or destroyed through the action of serine proteases in collected blood. Blood components that can be measured in blood collected by the method of the present invention include, but are not limited to, soluble fibrin, fibrinogen, fibrinopeptide A, factor VIII, factor V, factor VII, activated factor VII, protein C, activated protein C, antithrombin III, D-dimer, C1-esterase, C3b. The process may also be suited for collecting samples for peptide hormones and glucosylated hemoglobins.

If during collection of a blood sample the pH of the blood is immediately lowered from the physiological pH 7.3 to a pH of between approximately 5.0 and 6.5, several advantages for the stability of the blood components can be gained without introducing the disadvantages or inconveniences found in published procedures where the blood is first collected using prior art anticoagulants that do not appreciably alter the blood pH and then acidified.

According to one embodiment of the present invention, blood is drawn into a container that contains one part citrate buffer. The final pH of the collected blood should preferably be between approximately 5.0 to 6.5. The citrate buffer should preferably contain between 0.3 to 0.6 mol/L citrate and have a pH of approximately 3.0 to 5.5 to which 5 to 15 parts by volume of blood is added during collection. The final concentrations of citrate buffer in the blood after mixing should be between approximately 0.05 to 0.1 mol/L. A preferred final concentration of citrate buffer in the blood after mixing is between approximately 0.065 to 0.085 mol/L with an especially preferred final concentration of between approximately 0.075 mol/L.

Preferably, the present invention includes collecting blood in various different citrate buffer compositions in which blood samples were collected as described above. For example, to further limit dilution of blood, 9.8 volumes of blood could be collected in 0.2 volumes of approximately 2 mol/L citrate buffer with a pH of about 4 to give a final blood pH of about 6 and a blood plasma concentration of citrate of about 0.072 mol/L. If less blood is collected and the volume of buffer is the same, the pH of the collected blood will be lower.

It is also contemplated as part of the present invention a method of reducing hemolysis in collected blood comprising the steps of introducing blood into a container containing an effective amount of an acidic buffer so that the final pH of the blood is between approximately 5.0 and 6.5. A preferred final pH range is approximately 5.4 to 6.3 with a most preferred pH of approximately 6.0.

To further inhibit hemolysis of the red blood cells, a surface active copolymer can optionally be included in the solution into which the blood is being collected. It is to be understood that other Pluronic ® surfactants can be used in the present invention to prevent hemolysis.

The surface active copolymer has the following general formula:

wherein a is an integer such that the hydrophobe represented by (C₃H₆O) has a molecular weight of approximately 950 to 4000, preferably about 1750 to 3500, and b is an integer such that the hydrophile portion represented by (C₂H₄O) constitutes approximately 50% to 95% by weight of the compound.

The most preferred surface active copolymer has the following specific formula:

wherein the molecular weight of the hydrophobe (C₃H₆O) is approximately 1750 and the total molecular weight of the compound is approximately 8400. This compound is sold under the trademark Pluronic ® F-68 (BASF Corporation, Parsippany, N.J.).

The optimal final concentration of surface active copolymer in the plasma of the collected blood is between approximately 0.01% to 0.1% (0.1 to 1 mg/mL).

In describing the utility of the present invention, a model blood component, a serine protease, tPA, was selected because it is unstable in blood collected by prior art methods. It is believed that the advantages of the present invention are that the rates of the reactions between tPA and PAI-1 and between tPA and other inhibitors of blood are reduced at a pH of about 5.0 to 6.5 as compared to the rates at the physiological pH of about 7.3. These reduced reaction rates will greatly increase the stability of tPA activity in plasma.

It is important to determine the tPA activity in the circulating blood and not the artifactually lower tPA activity found in stored blood samples collected according to the prior art. Thus, the present invention will improve the value of measuring tPA activity to diagnose the etiology of thrombotic disease, the risk of developing thrombotic disease or the tPA activity obtained during tPA therapy. Similar mechanisms apply to other serine proteases and serine protease inhibitors and to protein components that are generated or destroyed by the action of serine proteases.

The present invention also includes a collection device comprising a container with the appropriate buffer so that when blood is introduced into the container, the blood will be acidified in such a way the blood is immediately mixed resulting in an immediate lowering of the blood pH to between 5.0 to 6.5. Preferably the container is a tube that can be manufacture from various materials including, but not limited to, glass and plastic. The tube can also have a stopper through which the blood can be introduced. The container can also be a syringe which contains the appropriate acidic buffer. Blood can be collected by puncturing an appropriate blood vessel with a hypodermic needle and drawing the blood into the container with the acidic buffer. In this way the blood is immediately mixed with the buffer resulting in the lowering of the pH to between 5.0 and 6.5. The amount of buffer that is contained in the container should be adjusted so that the final ratio of buffer to blood is between approximately 2:8 and 0.1:9.9. This means that for the preferred ratio of buffer to blood, 1:9, the tube, when filled with blood, will have 9 parts of blood to 1 part buffer. It is also contemplated that the buffer can be a solid buffer substance in the container.

The preferred method of collecting blood for measuring tPA activity comprises collecting the blood in a container containing a citrate buffer at an acidic pH. The preferred buffer comprises approximately 0.5 mol/L sodium citrate at a pH of approximately 4.3. Good tPA stability is found at a final pH range of approximately 5.0 to 6.5 with a preferable range of 5.4 to 6.3 with a most preferred pH of approximately 5.8. These conditions are mild indicating that this approach is valuable for other analytes, e.g., soluble fibrin, fibrinogen, fibrinopeptide A, factor VIII, factor V, factor VII, activated protein VII, protein C, activated protein C, antithrombin III, D-dimer, C1-esterase, C3b. The process may also be suited for collecting samples for peptide hormones and glucosylated hemoglobins.

In addition, the method according to the present invention preserves soluble fibrin levels in blood and plasma samples thereby improving the diagnostic importance of this assay. High levels of soluble fibrin are found in the blood of patients with malignancies, risk pregnancies, sickle cell anemia crises and in patients suffering from severe trauma. High levels of soluble fibrin is also a symptom of disseminated intravascular coagulation.

Thus, the present invention of lowering the pH of blood during collection greatly improves the stability in the blood components in the sample and in the plasma sample derived thereof. These components include, but are not limited to, several important fibrinolytic parameters namely tPA activity, PAI-1 activity and soluble fibrin.

It is contemplated that another embodiment of the present invention is control plasma made by collecting blood in a container in which an effective amount of an acidic buffer is present so that the final pH of the blood is between approximately 5.0 and 6.5. The control plasmas provide a method for producing reliable reference standards for determining the concentration of components in blood.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE I

The following example describes how the pH of the blood can be immediately lowered to the range of 5.0 to 6.5 without causing excessive hemolysis.

Citric acid monohydrate, $M_r=210$, and trisodium citrate dihydrate, $M_r=294$, is obtained from Merck Damstadt, W. G. The surface active copolymer, Pluronic ® F-68, is obtained from BASF Corporation, Parsipanny, N.J. Blood is obtained by vein puncture and collected on 0.13 mol/L trisodium citrate (1 part citrate buffer to 9 parts blood) in a siliconized Venoject ® collection tube.

0.5 mol/L solutions of citric acid and of trisodium citrate are mixed to give 0.5 mol/L sodium citrate solutions with pH of 4.0, 4.5, 5.0 and 5.5. Each of these solutions is aliquoted and a small volume of concentrated F68 solution (25%) is added to give final concentrations of 0, 0.1 or 1% by weight.

1.0 mol/L and 2.0 mol/L citrate buffers pH 4.0, 4.5, 5.0 and 5.5 containing 0.1 or 1% F68 are made accordingly.

Citrated blood is dispensed in 300 μL aliquots to which 33 μl of each of the 36 different buffers are added, mixed and incubated at room temperature (22° C.) for 20 hours. The samples are centrifuged six minutes at 1500×g, diluted six fold in 0.15 mol/L NaCl and subjected to pH and absorptivity at 537 nm determination. The absorption value (optical density at 1 cm path length) is multiplied by the dilution factor of 6.

For practical reasons, the experiment is performed with anticoagulated blood. However, this is expected to have little or no impact on the results. The results are shown in Table 1.

Table 1 shows pH and absorption at 537 nm for plasma obtained from blood samples to which 1:9 volume of citrate buffers with various concentrations, pH and F68 content are added.

TABLE 1

|  | 0.5 mol/L Citrate Conc. F68 (mg/mL) | | | 1.0 mol/L Citrate Conc. F68 (mg/mL) | | | 2.0 mol/L Citrate Conc. F68 (mg/mL) | | |
| --- | --- | --- | --- | --- | --- | --- | --- | --- | --- |
| pH | 0 | 1 | 10 | 0 | 1 | 10 | 0 | 1 | 10 |
| 4.0 pH | 5.62 | 5.50 | 5.58 | 4.88 | 4.90 | 4.94 | 4.62 | 4.58 | 4.60 |
| A | 0.54 | 0.51 | 0.75 | 4.61 | 3.32 | 2.24 | 10.92 | 10.5 | 11.6 |
| 4.5 pH | 6.07 | 6.04 | 6.09 | 5.48 | 5.44 | 5.41 | 5.08 | 5.10 | 5.10 |
| A | 0.62 | 0.56 | 0.55 | 0.61 | 0.49 | 0.46 | 5.24 | 1.09 | 1.40 |
| 5.0 pH | 6.50 | 6.48 | 6.52 | 5.92 | 5.83 | 5.90 | 5.58 | 5.51 | 5.53 |
| A | 0.67 | 0.73 | 0.678 | 0.53 | 0.48 | 0.44 | 0.92 | 0.92 | 0.91 |
| 5.5 pH | 6.78 | 6.83 | 6.92 | 6.34 | 6.33 | 6.35 | 6.02 | 5.93 | 5.99 |
| A | 0.72 | 0.68 | 0.65 | 0.84 | 0.70 | —* | 0.51 | 1.10 | 1.29 |

*not determined

As can be seen from Table 1, the addition of the surface active copolymer to the freshly collected blood reduces the hemolysis (lyses of the red blood cells) as indicated by the absorbance at 537 nm. This observation is particularly clear with the addition of 1 mol/L citrate at a pH of 4.0 and with the addition of 2 mol/L citrate at a pH of 4.5. In both cases, there is an increase in the stability of the red blood cell membranes as shown by the decrease of absorbance at 537 nm as the surface active copolymer concentration increases.

EXAMPLE II

The following experiment shows that stabilization of tPA activity can be obtained by practicing the method of blood collection of the present invention.

Venoject ® (Teruno Europe, Lewen, Belgium) are evacuated siliconized glass tubes containing 0.5 mL 0.13 mol/L trisodium citrate and will draw 4.5 ml of blood. In this example, this is hereinafter called "Venoject regular". Some "Venoject regular" are modified as an embodiment of the present invention. The citrate buffer in the "Venoject regular" tubes are removed by suction with a hypodermic needle and 0.5 mL 1.0 mol/L citrate buffer pH 4.0 is introduced through the rubber stopper with a hypodermic needle. In this way, the citrate buffer content is changed without disturbing the vacuum in the tube. The modified tubes are hereinafter called "Venoject modified".

Blood is drawn by vein puncture from an apparently healthy individual into two "Venoject regular" and into two "Venoject modified" tubes. To each of one "Venoject regular" and one "Venoject modified" tubes, 4 μl of 500 IU/mL of single chain t-PA dissolved in 1.0 mol/L $KHCO_3$ is added. This results in an increase in tPA activity by about 8.9 IU/mL in the plasma at a hematocrit of 0.45. The four tubes, "Venoject regular", "Venoject regular+tPA", "Venoject modified" and "Venoject modified+tPA" are incubated at room temperature (22° C.) and 1 mL aliquots are drawn after 0.25, 1, 2 and 3 hours. The aliquots are centrifuged six minutes at 1500×g and 100 μl plasma is acidified by addition of 100 μl mol/L acetate buffer pH 3.9 and analyzed according to the protocol of Wiman, et al.

*Clin. Chem. Act.* 127: 279-288 (1983) using Spectrolyse TM /fibrin reagents from Biopool AB, Umeå, Sweden. The results of the study are shown in Table 2.

In Table 2, tPA activity in blood plasma is measured after blood sample collection in "Venoject regular" and "Venoject modified" with and without addition of about 9 IU/mL tPA at time zero. The blood is incubated at room temperature for 0.25, 1,2 and 3 hours before separation of the blood cells. tPA activity is expressed in IU/mL.

TABLE 2

| Time Hours | Venoject Regular | Venoject Regular and tPA | Venoject Modified | Venoject Modified and tPA |
|---|---|---|---|---|
| 0.25 | 0.51 | 3.8 | 1.3 | 8.4 |
| 1 | 0.14 | 1.7 | 1.6 | 9.6 |
| 2 | 0.07 | 0.6 | 1.4 | 9.6 |
| 3 | 0.04 | 0.4 | 1.4 | 9.9 |

As seen in Table 2, tPA is stable in Venoject modified tubes while tPA activity in unmodified tubes decreases rapidly.

EXAMPLE III

In the following example, blood collection according to the present invention is compared with a prior art method of collecting blood. The example demonstrates that stabilization of tPA activity can be obtained without the inconvenience of excessive hemolysis.

4.5 mL of blood is collected in 0.5 mL of sodium citrate buffer in siliconized glass tubes from healthy subjects. In each of 22 different buffers (citrate buffers ranging from 0.13 to 0.8 mol/L, pH range from approximately 3 to 5.5) blood from 5 individuals is collected. The blood is aliquoted, 3×1.5 mL, into capped polystyrene tubes, incubated at 22° C. for 0.05, 1 and 4 days. Plasma is obtained by centrifugation for 10 minutes at 3000×g, frozen and stored at −20° C. tPA activity is determined with a fibrin stimulated chromogenic substrate assay (Spectrolyse TM /fibrin, Biopool AB, Umeå, Sweden). The mean tPA activity half life ($t_{\frac{1}{2}}$) is then determined. The pH is measured with a standard glass electrode. Hemolysis determined as increase in absorbance at a wavelength of 540. Experiments are performed with 22 different buffers (citrate buffers with varying concentration from 0.13 to 0.8 mol/L and pH ranging from 3.0 to 5.5. The detailed results of one of these experiments using 0.5 mol/L citrate buffer pH 4.0 is provided in FIG. 1 and Tables 3 and 4.

TABLE 3 tPA activity in plasma (IU/mL) from blood stored at room temperature

| | 0.5 mol/L citrate pH 4.0 | | | 0.13 mol/. citrate | | |
|---|---|---|---|---|---|---|
| subj. | day 0 | day 1 | day 4 | day 0 | day 1 | day 4 |
| 1 | 0.9 | 0.8 | 0.6 | 0.1 | 0 | 0 |
| 2 | 1.2 | 1.0 | 0.9 | 0.4 | 0.1 | 0 |
| 3 | 1.1 | 1.1 | 0.8 | 0.5 | 0 | 0 |
| 4. | 0.7 | 0.7 | 0.7 | 0 | 0 | 0 |
| 5 | 1.0 | 1.0 | 0.8 | 0.4 | 0 | 0 |

TABLE 4

Absorbance at 540 nm in plasma from blood stored at room temperature

| | 0.5 mol/L citrate pH 4.0 | | | 0.13 mol/. citrate | | |
|---|---|---|---|---|---|---|
| subj. | day 0 | day 1 | day 4 | day 0 | day 1 | day 4 |
| 1 | 1.4 | 1.7 | 2.7 | 1.1 | 1.3 | 2.1 |
| 2 | 0.2 | 0.4 | 3.2 | 0.2 | 0.7 | 0.8 |

TABLE 4-continued

Absorbance at 540 nm in plasma from blood stored at room temperature

| | 0.5 mol/L citrate pH 4.0 | | | 0.13 mol/. citrate | | |
|---|---|---|---|---|---|---|
| subj. | day 0 | day 1 | day 4 | day 0 | day 1 | day 4 |
| 3 | 0.6 | 0.7 | 3.0 | 0.8 | 0.3 | 1.3 |
| 4. | 1.9 | 1.4 | 4.9 | 1.3 | 1.1 | 2.4 |
| 5 | 0.4 | 0.3 | 3.6 | 0.8 | 1.0 | 1.1 |

Figure 1:
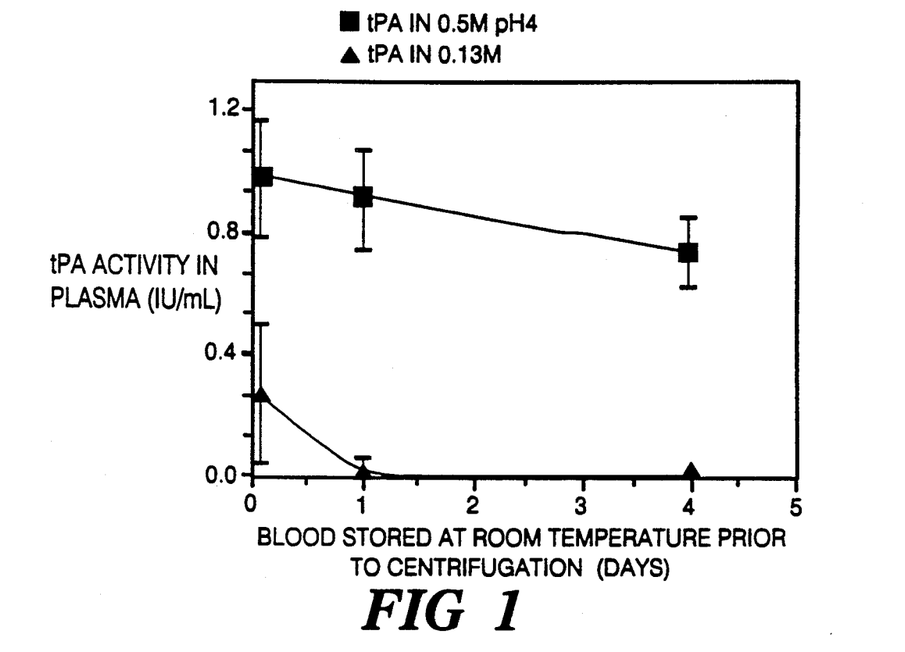
FIG. 1 shows tPA activity in blood collected in two buffers.

FIG. 1 and Table 3 show tPA activity in blood at 0.05, 1 and 4 days after collection in this buffer, 0.5 mol/L at pH 4.0, and in conventional 0.13 mol/L trisodium citrate buffer. As shown in FIG. 1, the tPA activity in blood collected in acidic buffer is more stable than tPA in blood collected in the conventional buffer. The final pH of the blood sample is approximately 5.5 as compared to 8.3 with the conventional 0.13 mol/L trisodium citrate buffer. Table 4 shows hemolysis in the two buffer systems. As shown, the hemolysis in the acidic buffer composition is acceptable.

Table 3 shows that tPA activity in blood collected according to the present invention is stable. In blood collected by a conventional method, the tPA activity declined rapidly.

EXAMPLE IV

This example shows that the tendency for hemolysis in collected blood is a function of blood pH and buffer concentration. Conditions for minimal hemolysis are established. Data generated in the study described in Example III is shown in Table 5.

TABLE 5

| Exp. No | Citrate (M) | Initial pH | Final pH | Relative Hemol. | tPA 1 hr (IU/mL) | tPA $t_{\frac{1}{2}}$ |
|---|---|---|---|---|---|---|
| 2 | 0.5 | 3.0 | 4.90 ± 0.07 | 72 | 1.1 ± 0.2 | |
| | 0.5 | 4.0 | 5.55 ± 0.06 | 4.9 | 1.0 ± 0.2 | 10.9 |
| | 0.3 | 3.0 | 5.58 ± 0.08 | 6.2 | 1.2 ± 0.2 | 4.6 |
| | 0.3 | 4.0 | 6.32 ± 0.13 | 0.7 | 1.0 ± 0.2 | 1.5 |
| | 0.13 | 2.3 | 7.10 ± 0.20 | 0.6 | 0.8 ± 0.4 | |
| | 0.13 | 3.0 | 7.54 ± 0.15 | 0.9 | 0.6 ± 0.2 | |
| | 0.13 | 8.3 | 8.38 ± 0.04 | 1.0 | 0.3 ± 0.2 | |
| 4 | 0.4 | 3.5 | 5.44 ± 0.09 | 10.8 | 0.7 ± 0.2 | −11.3 |
| | 0.4 | 4.0 | 5.68 ± 0.04 | 2.6 | 0.6 ± 0.2 | 5.5 |
| | 0.35 | 4.0 | 5.96 ± 0.09 | 0.7 | 0.6 ± 0.2 | 1.2 |
| | 0.4 | 4.5 | 6.08 ± 0.08 | 0.4 | 0.6 ± 0.2 | 2.2 |
| | 0.13 | 8.3 | 8.02 ± 0.08 | 1.0 | 0.2 ± 0.1 | |
| 5 | 0.45 | 4.0 | 5.72 ± 0.08 | 4.8 | 0.7 ± 0.3 | 5.1 |
| | 0.55 | 4.5 | 5.80 ± 0.07 | 2.5 | 0.7 ± 0.3 | 4.4 |
| | 0.6 | 5.0 | 6.24 ± 0.05 | 0.4 | 0.7 ± 0.2 | 4.4 |
| | 0.5 | 5.0 | 6.60 ± 0.07 | 0.8 | 0.5 ± 0.3 | |
| | 0.4 | 5.0 | 6.92 ± 0.13 | 0.7 | 0.4 ± 0.2 | |
| | 0.3 | 5.0 | 7.34 ± 0.15 | 0.6 | 0.5 ± 0.1 | |
| | 0.13 | 8.3 | 8.06 ± 0.05 | 1 | 0.1 ± 0.1 | |
| 7 | 0.55 | 4.0 | 5.40 ± 0.07 | 40 | 0.8 ± 0.2 | −23 |
| | 0.65 | 4.4 | 5.52 ± 0.08 | 36 | 0.7 ± 0.2 | −14 |
| | 0.5 | 4.5 | 5.94 ± 0.11 | 5.7 | 0.7 ± 0.3 | 2.9 |
| | 0.13 | 8.3 | 8.20 ± 0.07 | 1 | 0.0 ± 0.0 | |

From each of five individuals, 9 volumes of blood is drawn in one volume of acidic citrate buffer characterized by its citrate concentration and its ph (initial pH). Anticoagulated blood is incubated at room temperature and plasma separated at various time points. The pH of the plasma (final pH), the degree of hemolysis (relative to that in conventional 0.13 mol/L tri-citrate pH 8.3), and the tPA activity is determined. Average values and the standard deviation for the five individuals is given in Table 5. The tPA activity half life (tPA $t_{\frac{1}{2}}$) is expressed in days.

The tPA activity half-life is found to be highly dependent on final pH but not on buffer strength. The decay of tPA activity in blood at acidic pH shows a linear relationship in a lin-log plot and can be characterized by a tPA activity half life value. Decay of tPA activity at pH above 6.4 shows a curvature and is not well defined by a half-life value. Only data sets that yield straight lines in lin-log plots is indicated with a half life value in Table 5. Negative tPA half life is found at pH values in the range of 5.4 to 5.5. This denotes that the tPA activity increases which could be due to dissociation of tPH/inhibitor complexes.

Figure 2:
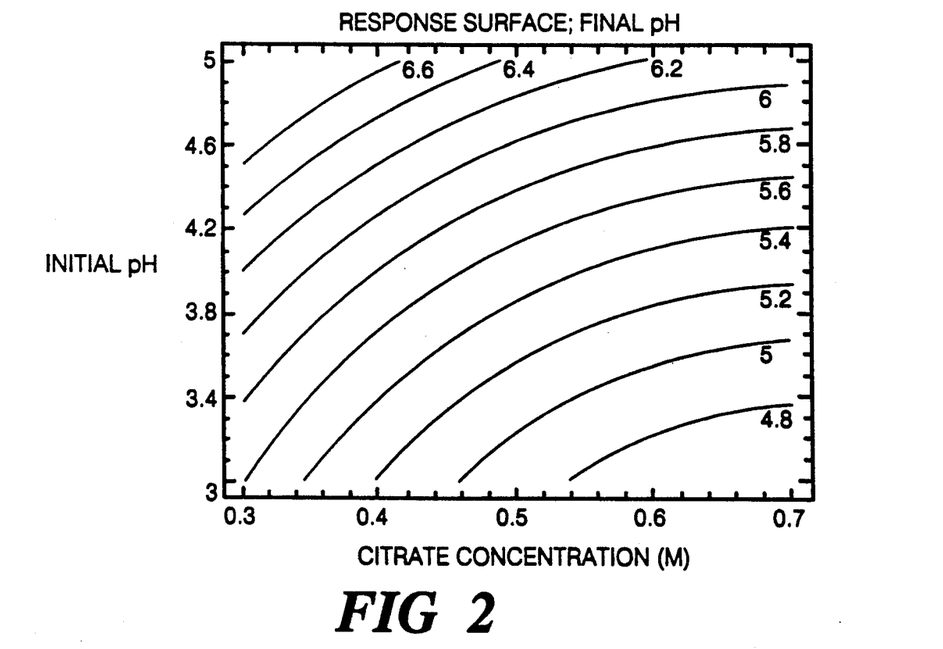
FIG. 2 shows the citrate buffer concentration and its pH (initial pH) treated as independent variables and the pH of the blood that was collected on that buffer (final pH), as dependent variable. A model of the response surface is obtained by fitting a second order polynomial function to the final pH. The data is from Table 5 herein.
Figure 3:
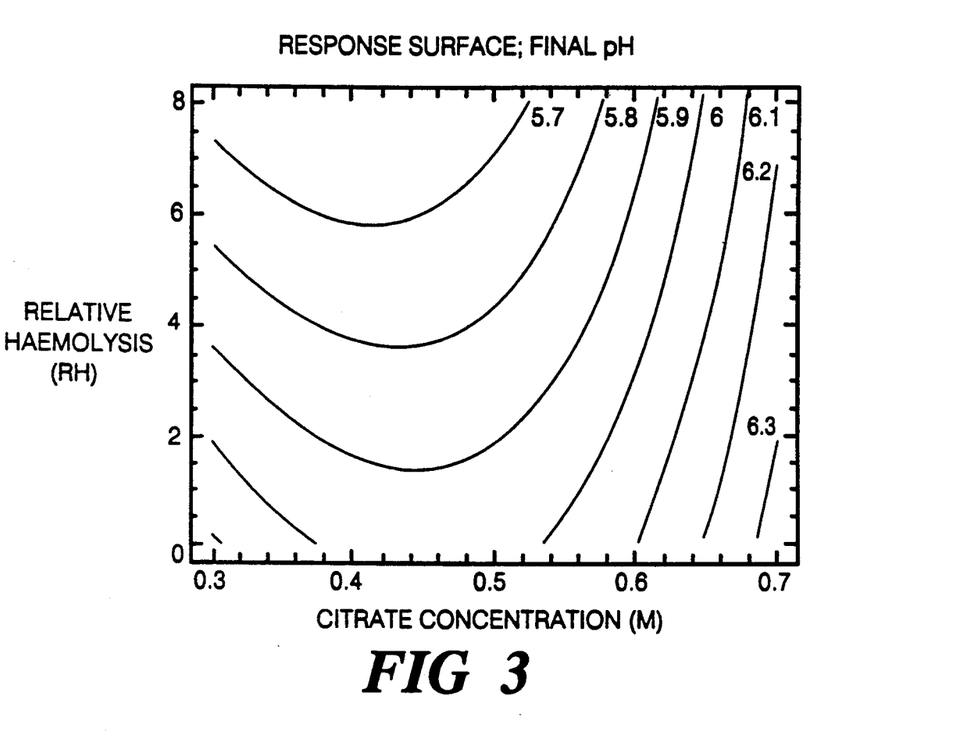
FIG. 3 is the same type of treatment of data as in FIG. 2. The dependent variable (final pH) is fitted to a second order polynomial function of the independent variables (citrate buffer concentration and relative degree or hemolysis. The data is from Table 5 herein.

To better understand how final plasma pH, hemolysis, citrate buffer concentration and buffer pH are interrelated, the response surface for one of them is fitted to a second degree polynominal function of two of the others. FIG. 2 shows how the final pH of the blood varies with buffer strength and initial pH (buffer pH). In FIG. 3, the final pH is treated as a function of citrate buffer concentration and the degree of hemolysis. This model shows a minima between 0.3 and 0.6 mol/L citrate. If a certain pH is to be reached with a minimum of hemolysis then FIG. 2 indicates the optimum buffer strength and FIG. 3 indicates the optimum buffer pH.

Figure 4:
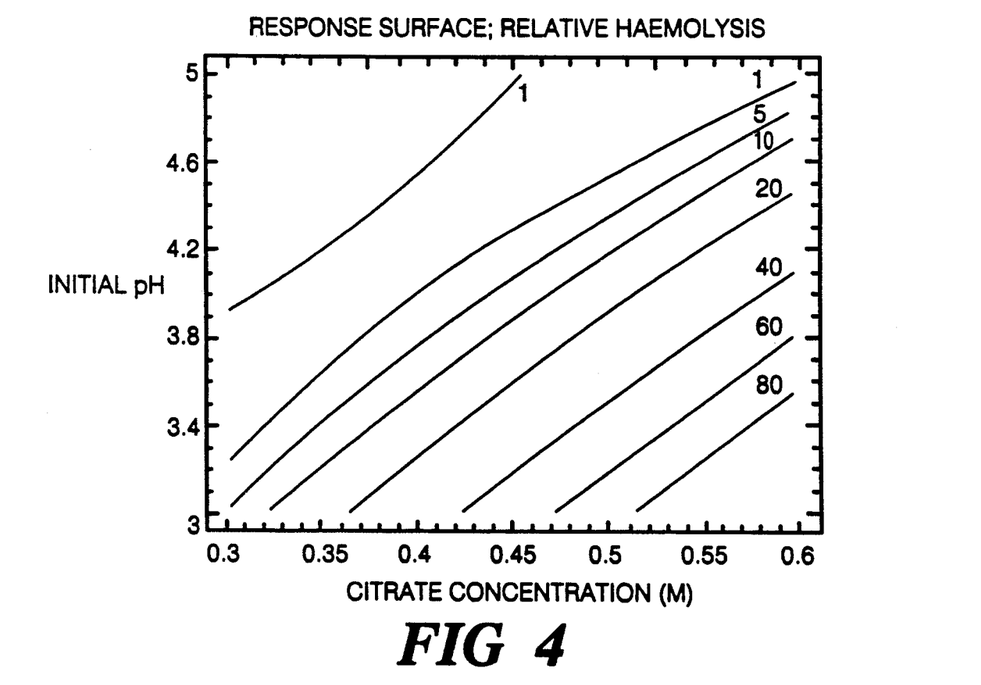
FIG. 4 is the same type of treatment of data as in FIG. 2 and 3. The relative degree of hemolysis is treated as a dependent variable and citrate buffer concentration and its pH as independent variables.

When hemolysis is plotted as a function of citrate buffer concentration and initial pH, FIG. 4, a valley of low hemolysis is found in about the same position as the line for pH 6.0 in FIG. 2. It appears that a global hemolysis minimum has been located. Collection of nine volumes of blood in one volume of 0.45 mol/L citrate buffer at a pH of 4.4 is indicated to give less hemolysis than any other one volume of citrate. The data in Table 5 indicate that the degree of hemolysis at this global minimum is about 40% that of the degree of hemolysis experienced in conventional citrate buffers. (i.e., 0.13 m/l trisodium citrate at pH 8.3).

EXAMPLE V

This example describes how a control plasma for measuring soluble fibrin is prepared.

Human plasma adjusted to pH 5.7 is obtained by drawing 9 volumes of blood from healthy subjects into 1 volume of 0.5 mol/L sodium citrate buffer pH 4.3 and isolating plasma by centrifugation for 15 minutes at $2000 \times g$. Since the pH of this plasma is 5.7, it is called "Normal plasma pH 5.7". The soluble fibrin content of this plasma is undetectable by the metod of Wiman, B. and Rånby, M., *Thromb. Haemostas*, 55: 58-66 (1986).

A concentrated solution of fibrin monomer in solution is prepared by digesting fibrinogen (Imco Corporation, Stockholm, Sweden) with bathroxobin (Pentapharm AG, Basel, Switzerland) in the presence of the fibrin polymerization inhibitor peptide Cly-Pro-Arg-Pro. The fibrinogen is dissolved to a defined concentration in the range 10 to 20 g/L in 0.3 mol/L NaCl containing Gly-Pro-Arg-Pro in the range 2 to 4 g/l to which a small volume of stock solution, about 100 BU/mL, of bathroxobin is added to give a final bathroxobin concentration in the range 0.05 to 0.1 BU/mL. The digestion is performed at room temperature, about 22° C., and is monitored by testing for fibrin monomer concentration by diluting an aliquot of the digest 500 fold in the normal plasma pH 5.7 and determining soluble fibrin content according to the method of Wiman, B. and Rånby, M., *Thromb. Haemostas.*, 55: 58-66 (1986). The digestion is terminated when the fibrin monomer concentration levels off. The monomer concentration is then the same as the original fibrinogen concentration.

Control plasma (also called reference plasma, plasma standard, or calibration plasma depending upon use) with a defined concentration of soluble fibrin is prepared by adding a small volume of the fibrin monomer solution to a relatively large volume of the normal plasma pH 5.7. For example, if the fibrin monomer concentration is 15 g/L (44.1 μmol/L) then addition of 50 μl of this to 10.0 mL of normal human plasma pH 5.7 will give a reference plasma containing 74.6 mg/L (219 nmol/L) of soluble fibrin. The control plasma may be diluted with normal human plasma pH 5.7 to give references plasmas with lower concentrations.

EXAMPLE VI

This example describes how control plasma for tPA activity is prepared.

Control plasma (also called reference plasma, plasma standard, or calibration plasma depending upon use) can be prepared by simply analyzing the normal plasma pH 5.7 prepared as described in Example 1 to tPA activity using the Wiman, B. et al, *Clin. Chim. Acta*, 127: 273-288 (1983). Typically, this value is 0.5 IU/mL as compared to the standard preparation 86/670 distributed by National Institute of Biological Standards and Control, Blanche Lane, South Mimms, Potters Bar, Hertfordshire, England.

Reference plasma with higher levels of tPA activity than that found in the normal plasma pH 5.7 can be prepared by adding a small volume of purified tPA with a well defined tPA concentration to the normal plasma pH 5.7 and again determining the tPA activity content.

EXAMPLE VII

This example demonstrates using the blood collection method of the present invention with a solid buffer substance.

Sodium citrate buffer with a buffer strength of 0.5 mol/L and pH 4.3 is prepared. Of this buffer solution, 0.5 mL of this buffer solution is aliquoted into 7 mL glass siliconized blood collection tubes. The tubes are placed in a lyophilizer and the contents are freeze dried. The tubes, now containing a cake of fine crystalline solid powder with low moisture content, are evacuated to about 190 mm Hg and sealed with a rubber top.

A hypodermic needle connected to a piece of rubber tubing is inserted into the top of the tube. Blood from the antecubital vein of healthy volunteers is drawn into the tubes. A maximum of about 2.3 mL is drawn in some tubes and 4.5 mL of blood is drawn in other tubes. The blood that flows into the tubes rapidly dissolves the fine crystalline material in the tubes upon which the pH of the is reduced. In the tubes that contained 4.5 mL of blood, the pH is rapidly reduced to about 5.7. In the tubes in which 2.3 mL had been collected, the pH is rapidly lowered to about 5.2.

It should be understood that the foregoing relates only to a preferred embodiment of the present invention and that numerous modifications or alterations may be made without departing from the spirit and scope of the invention as set forth in the appended claims.

We claim:

1. A method of measuring tissue plasminogen activator comprising the steps of:
   a. introducing whole blood into a container containing an effective amount of an acidic buffer so that the final pH of the blood is between approximately 5.0 and 6.5; and
   b. measuring the tissue plasminogen activitor.

2. The method of claim 1 wherein the final pH of the blood is between approximately 5.4 and 6.3.

3. The method of claim 2 wherein the final pH of the blood is approximately 5.8.

4. The method of claim 1 wherein the buffer is selected from the group consisting of citrate buffer, acetate buffer, propionate buffer, borate buffer, isocitrate buffer, aconitate buffer, and oxalate buffer.

5. The method of claim 4 wherein the buffer is a citrate buffer.

6. The method of claim 5 wherein the citrate buffer is sodium citrate.

7. The method of claim 1 wherein the ratio of buffer to blood is less then 1:4 by volume.

8. The method of claim 7 wherein the ratio of buffer to blood is approximately 1:9 by volume.

9. The method of claim 1 wherein the buffer is a solid buffer.

10. The method of claim 1, wherein the acidic buffer further comprises an amount of a surface active copolymer which is effective in reducing hemolysis with the following general formula:

$$HO(C_2H_4O)_b(C_3H_6O)_a(C_2H_4O)_bH$$

wherein a is an integer such that the hydrophobe represented by $(C_2H_6O)$ has a molecular weight of approximately 950 to 4000 and b is an integer such that the hydrophile portion represented by $(C_2H_4O)$ constitutes approximately 50% to 95% by weight of the compound.

11. The method of claim 10, wherein the surface active copolymer has the following general formula:

$$HO(C_2H_4O)_b(C_3H_6O)_a(C_2H_4O)_bH$$

wherein a is an integer such that the hydrophobe represented by $(C_3H_6O)$ has a molecular weight of approximately about 1750 to 3500 and b is an integer such that the hydrophile portion represented by $(C_2H_4O)$ constitutes approximately 50% to 95% by weight of the compound.

12. The method of claim 11 wherein the surface active copolymer has the following formula:

$$HO(C_2H_4O)_b(C_3H_6O)_a(C_2H_4O)_bH$$

wherein the molecular weight of the hydrophobe $(C_3H_6O)$ is approximately 1750 and the total molecular weight of the compound is approximately 8400.

13. The method of claim 1 wherein the final concentration of the buffer in the plasma of collected blood is between approximately 0.05 and 0.1 mol/L.

14. The method of claim 13 wherein the final concentration of the buffer in the plasma of collected blood is between approximately 0.065 and 0.085 mol/L.

15. The method of claim 14 wherein the final concentration of the buffer in the plasma of collected blood is approximately 0.075 mol/L.

* * * * *